United States Patent [19]

Åström et al.

[11] 4,343,179

[45] Aug. 10, 1982

[54] UTILITY POLE HARDNESS TESTER

[76] Inventors: Göta L. Åström, 12 Lämmeltåget, Luleå, Sweden, S-951 46; Sigvard N. Johansson, 30 Söderbyvägen, Västerhaninge, Sweden, S-137 80

[21] Appl. No.: 210,260

[22] Filed: Nov. 25, 1980

[30] Foreign Application Priority Data

Nov. 27, 1979 [SE] Sweden ................................ 7909777
Nov. 17, 1980 [SE] Sweden ................................ 8008054

[51] Int. Cl.$^3$ ............................................... G01N 3/48
[52] U.S. Cl. ......................................................... 73/81
[58] Field of Search ............................................ 73/81

[56] References Cited

U.S. PATENT DOCUMENTS 2,389,030 11/1945 Dana ........................................ 73/81
4,249,414 2/1981 Barth ....................................... 73/81

FOREIGN PATENT DOCUMENTS 2638261 3/1977 Fed. Rep. of Germany .......... 73/81

Primary Examiner—S. Clement Swisher
Attorney, Agent, or Firm—Burns, Doane, Swecker & Mathis

[57] ABSTRACT

The invention relates to a test device, by means of which power poles are tested for hardness or rot depth. The device comprises a frame portion and a test needle or corresponding member located therein or thereto. The test needle is to be exposed to an actuation force so as to penetrate into the pole material. The degree of penetration for a definite actuation force is a measure of the hardness or rot depth. The test device further comprises means to be exposed to actuations, for example manual ones, by which means the actuation force to the penetration portion can be produced. The frame portion is provided with a part, which entirely or partially can be driven into the ground base adjacent the pole. The exposed means extend with upper portions above the ground surface in order to permit actuations to produce the actuation force. At the upper portions of the exposed means indicating means are located which indicate the degree of penetration for a definite size of the actuation force.

14 Claims, 9 Drawing Figures

FIG.6
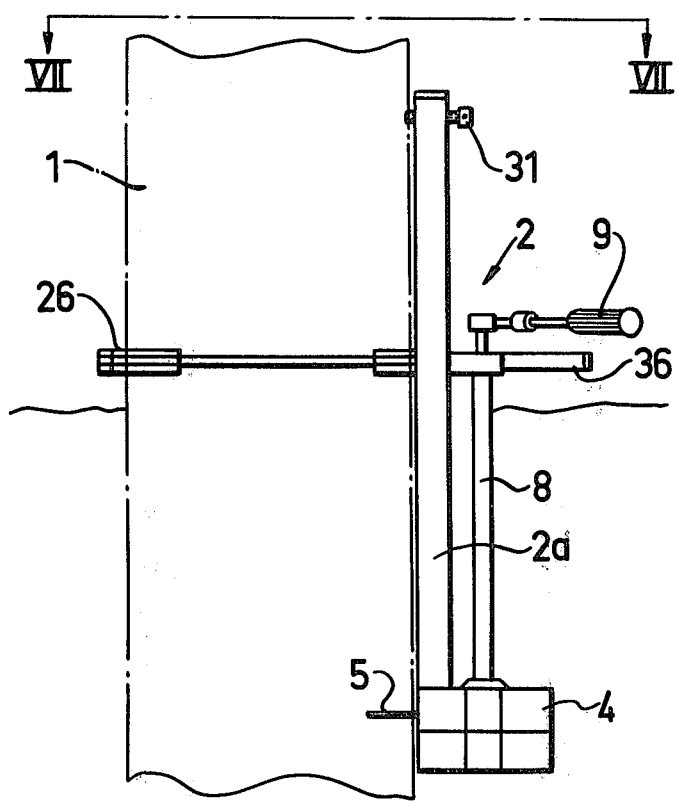
FIG.7
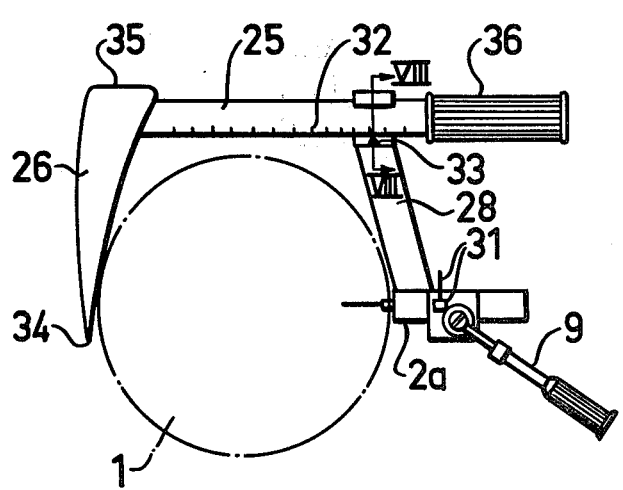
FIG.8

UTILITY POLE HARDNESS TESTER

BACKGROUND AND SUMMARY OF THE PRESENT INVENTION

This invention relates to a device for testing the hardness or rot depth of a power pole, for example a telephone pole, comprising a frame portion, a penetration portion located in or at the frame portion and intended, in response to an actuation force, to penetrate into the pole material, and members exposed to actuations, by which members the actuation force for the penetration portion is produced.

The new testing device is intended to be used for testing the rot depth and/or hardness in telephone poles or other corresponding power poles, such as power-line poles and the like. Such poles are made of wood and can be impregnated or unimpregnated. In the firstmentioned case salt-impregnated poles decaying from the outside are primarily of interest for the new device according to the invention.

The poles can have been sunk into the ground and are exposed to rotting in their buried portions, especially at the so-called earth band or at the pole portions located at the ground surface. As the poles much be climbed in connection with line work to be carried out high up on the poles, the rotting can involve risk of personal injuries. Regulations are, therefore, set up which prescribe the condition of the poles for being approved. This in its turn has given rise to the desire of being able to check in different connections the depth to which the rotting has proceeded.

The equipment, which heretofore has been used for testing rot depth or hardness, for example, of telephone poles have proved less practical. Test of a relatively great number of poles have been relatively complicated and expensive. For rendering the pole portions susceptible to rotting accessible, it was necessary to remove the soil and the possible wedging about each pole whereafter samples were taken in one or several points along the pole periphery and possibly in a vertical direction of the pole.

In accordance with the present invention, this is not necessary any longer. It is a characterizing feature of the invention, that a frame portion is provided with a part, which can be driven or sunk into the soil support adjacent the pole, and that the penetration portion, which has the shape of a pointed needle or the like, is placed in or at said part. The members for producing the actuation force, by which the penetration portion is controlled, are formed such that in the entirely or partially sunk state of said part, the members extend with their upper parts above the ground and from there it is possible by actuations to produce the actuation force. The invention also comprises the feature that the test device is provided with indicating means showing the degree of penetration of the penetration portion into the pole material when an actuation force of predetermined size is initiated above the ground.

In further embodiments, technical designs of different parts of the test device are proposed which increase the effect of the test tool, which is simple and economic to use in practice. The new test device is easy to handle and has a relatively light weight. The frame portion with associated measuring needle can be driven down, for example, by means of a sledge or some other corresponding tool and/or by mechanic beaters. When the pole is wedged by stones or the like, the frame portion can be driven down between the same.

BRIEF DESCRIPTION OF THE DRAWING

The invention is explained in the following by way of an embodiment described in the following and with reference to the accompanying drawings, in which FIG. 6 is a schematic view of a test device according to the invention provided with a modified clamping means, which device is driven down adjacent and clamped on a pole, FIG. 7 is a section along the line VII—VII in FIG. 6, and FIG. 8 is a section along the line VIII—VIII in FIG. 7.

DETAILED DESCRIPTION OF THE PREFERRED EMBODIMENT

Figure 1:
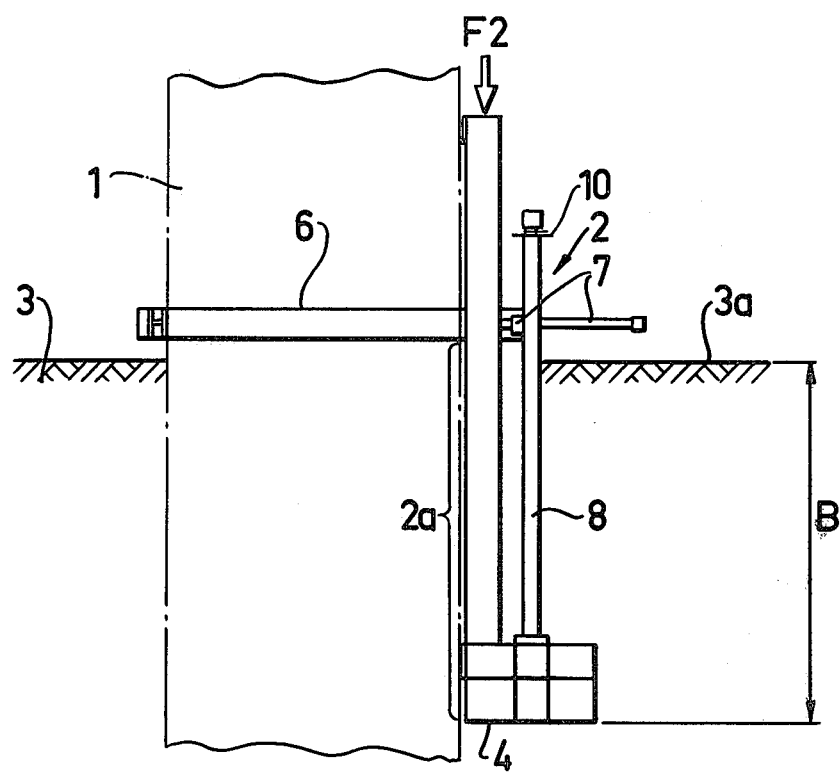
FIG. 1 is a schematic lateral view of the test device driven down adjacent and attached to a pole to be rot tested.
Figure 2:
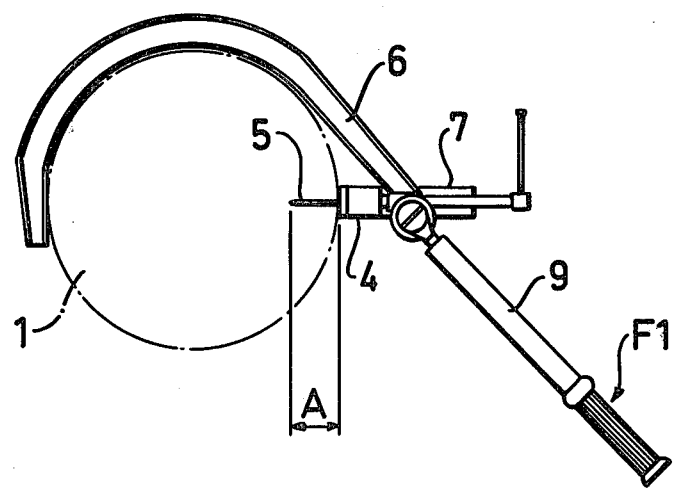
FIG. 2 is a view from above of the test device and pole according to FIG. 1.

As mentioned above, the test device can be used for testing possible rot depth in the wood material of the pole or to test the hardness thereof. In principle, a test needle or similar penetration member is used for this purpose. By measuring the distance through which the test needle penetrates into the pole at a predetermined actuation force, the hardness of the pole wood can be determined. Rot softens the pole material, and the greater the penetration depth of the needle into the pole for a definite force, the greater the decay can be assumed to be, and vice versa. A pole 1, for example a telephone pole, (FIGS. 1 and 2) may have an outer diameter of, for example, 150-250 mm and normally tapers upward. The test device 2 is to be driven down to the side of and adjacent the pole, which at the embodiment shown is sunk into a soil base 3, which may be of any occurring condition, for example sand, earth, clay, till etc. The test device is provided downwardly with a bearing housing 4 for a test needle 5. The bearing housing comprises a bearing for longitudinal movement of the needle, so that the needle can be actuated between a fully retracted position and a fully extended position. The total extension movement A for the test needle may be about 40 mm. A rot depth extending this value may imply that the pole must be scrapped, because the rot depth normally can be assumed to extend uniformly about the periphery. Non-uniform attacks, however, can occur, and, therefore, sampling in several points along the pole periphery normally is prescribed.

The test device, thus, comprises a part 2a (FIG. 1) to be sunk or driven into the ground base. The total driving depth B or length of the part 2a can vary. For example that it may be desirable to make rot tests at 300 mm. Tests, however, can be carried out at other levels, both deeper and higher and also above the ground surface. The test device also is provided with a clamp yoke 6 and an associated clamp 7. By means of these retaining means 6,7 the test device is fixed on the pole so that the bearing housing firmly abuts the shell surface of the pole, before the test needle is actuated. Other types of retaining or fixing means can be imagined, for example, a chain, wire etc. with associated tightening screw.

In order to actuate the test needle from above the ground level 3, the test needle is actuated via a longitudinal movement mechanism by means of a turning rod, which is supported in a bearing pipe 8. The bearing pipe is attached on the upper surface of the bearing housing 4 and substantially is in parallel with the part 2a. The bearing pipe, besides, extends freely to the side of the part 2a and is not coupled together therewith, in order to prevent undue actuation from the strokes in connection with the driving-down of the part 2a.

The turning rod projects upward above the bearing pipe at the upper part thereof, where the turning rod is attached to a dynamometric wrench 9 of a kind known per se. The wrench is commercially available and operates with a moment size, which at the embodiment shown is about 40 Kpcm. An example of such a wrench is "Wernmeter" 7042B.

At the upper portions of the bearing pipe 9 a graduated disc 10 is attached, and to the turning rod a turning needle is attached which follows the movement of the turning rod. The disc is graduated to indicate the distance of the test needle movement, i.e. 0–40 mm in the present case. A force F1 is applied to the dynamometric wrench, and the moment for which disengagement takes place in the wrench, is set in relation to the actuation force for driving the test needle into the pole material. The test device is driven down into the ground base with the force F2.

Figure 3A:
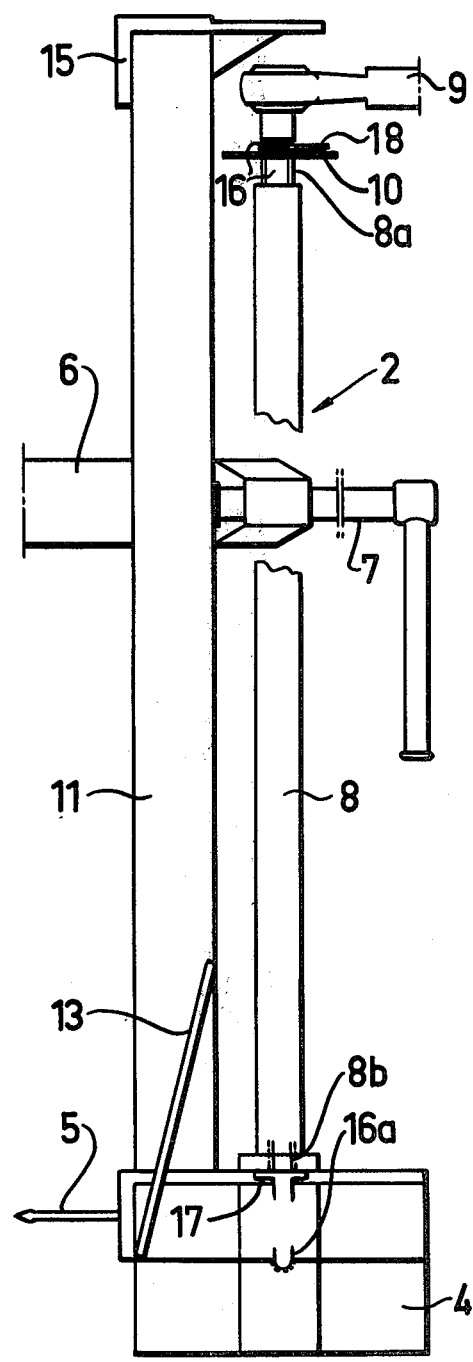
FIG. 3a is a vertical view of the test device.
Figure 3B:
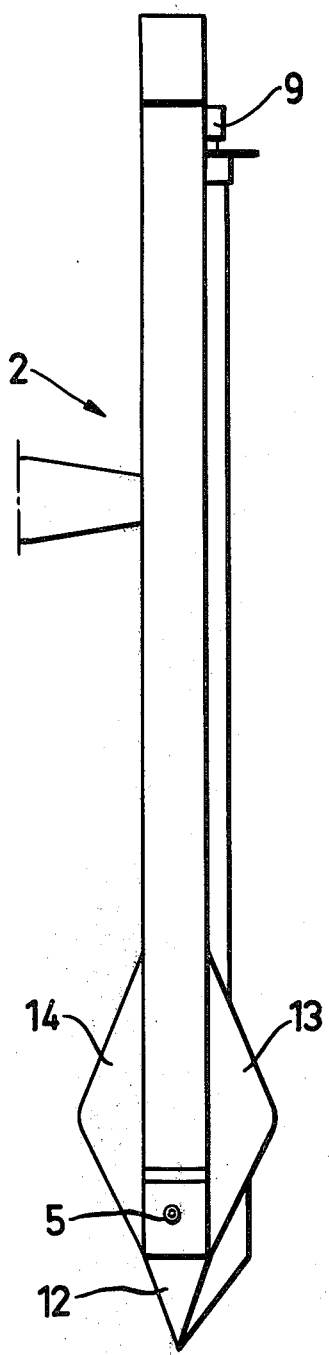
FIG. 3b is a vertical view of the test device turned through 90° in relation to the view according to FIG. 3a, FIG. 4 is a cross-sectional view of a rotary housing mechanism included in the test device.

The test device is shown in detail in FIGS. 3a and 3b. The frame portion 11 is made of steel. Downwardly the frame portion is integrated with the bearing housing 4. The frame portion 11 as well as the bearing housing have downwardly a wedge-shaped part 12, which facilitates the driving of the frame portion and bearing housing down into the ground base. The bearing housing has an oblong outer contour, which extends outwardly from the pole. At the lower end, the frame portion is provided with inclined members in the form of wings 13 and 14 so arranged, that the frame portion at its driving down adjacent the pole is forced to tightly abut the shell surface of the pole. The frame portion is upwardly provided with a stroke protection 15, which extends outward over the attachment of the dynamometric wrench. In this way, the wrench and the bearing pipe 8 and the turning rod mounted therein are not exposed to the driving strokes for the frame portion 1 in the event, that a stroke is misdirected. The stroke protection is made of impact resistant material, and the oblong frame (i.e. the test device in its entirety) may have a total length of about 500 mm.

The bearing pipe 8 is attached to the upper surface of the housing 4 by means of screws, by welding etc. The turning rod 16 is so mounted in the bearing pipe that it is rotatable by the dynamometric wrench and at the same time is fixed in its vertical position. The vertically fixed position is indicated by a transverse pin 17 where the turning rod projects out of the bearing pipe. The lower end surface 16a of the turning rod is supported in a cup in the bottom of the bearing housing. Bearing parts in the bearing pipe are designated by 8a and 8b. The transverse pin 17 co-operates with a lower surface on the bearing part 8b. The needle on the turning rod is designated by 18.

Figure 4:
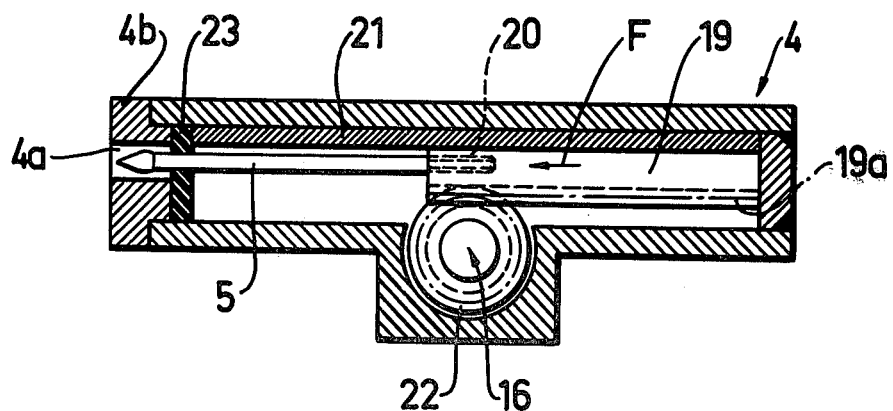

In the bearing housing 4 (FIG. 4) the test needle 5 is attached in a rack 19 movable in longitudinal direction. The test needle can be screwed into the rack end via threads 20, so that the test needle is exchangeable. The rack is mounted slidable in its longitudinal movement direction (in FIG. 4 from the right to the left, and vice versa) in a slide bearing 21, which may be designed in a manner known per se. The bearing 21 may have internal guide grooves, in which longitudinal shoulders on the rack are arranged. Teeth 19a on the rack 19 mesh with a gear wheel 22 attached to the turning rod 16. At the egress opening 4a of the bearing housing a wiper 23 of rubber, plastic or the like is located which prevents impurities from penetrating into the bearing housing when the test needle is retracted into the housing by the rack. The end part 4b is detachable, so that the wiper is exchangeable like the test needle.

Figure 5:
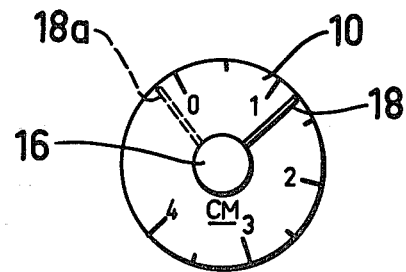
FIG. 5 is a schematic view of a graduated disc and an indicating needle associated with the test device.

As shown in FIG. 5, the disc 10 can be graduated in cm, for example between 0 and 4 cm. In the embodiment shown, the test needle is acute and owing to its point penetrates readily even into sound wood. When the needle thereafter penetrates in to a greater depth, the real resistance to the needle is obtained. In view thereof, the turning rod or indicating needle has a starting position 18a, which is located slightly before the O-position in order to compensate for the penetration of the point. In the position O the penetration proper commences. In the embodiment shown in FIG. 5 the test needle has penetrated in 1.2 cm for an actuation force F for the needle, which force is determined with the dynamometric wrench and with the transfer members formed by the turning rod 16, gear wheel 22 and rack 19, from which latter, thus, the actuation force F is obtained. The gear ratio on the transfer members as well as the size of the release moment in the wrench can be selected so that a suitable force F1 can be used on the wrench. During tests with the test device, the arm of the dynamometric wrench moves relatively uniformly and slowly so that variations in the penetration speed of the needle do not affect the result. The uniform and slow movement actuation must be tried out in every single case. The test device can be utilized for testing pole parts other than those located beneath the ground surface, in which case basically the same procedure is applied, except that the frame portion and bearing housing are not driven down into the ground base. The test needle 5 is made of a suitable metal, such as steel or the like.

With reference to FIGS. 6–8 a modified embodiment of the clamping means for the test device comprises a handle 25, which at one end is provided with a clamping leg 26 for engagement with the pole side remote from the frame 2a. The clamping leg 26 is clamped detachably in a partially open recess 27 at the end of a carrying arm 28. The arm 28 is attached to the frame 2a and has such a length, that the recess 27 is located to the side of the pole 1.

The recess 27 has a width corresponding to or slightly greater than the width of the handle with rectangular cross-section and is partially covered at one end by a flange 29 extending over the recess as shown in FIG. 8. The length of the recess should not exceed its width.

For attaching the clamping device, the handle 25 is inserted beneath the flange 29 of the recess and then turned down into the recess 27, whereafter the clamping leg 26 by help of the handle 25 is drawn against the pole 1 and at the same time the frame 2a is pressed inward against the same. Thereby the handle 25 is clamped in the recess 27 by the sides 30 thereof, owing to the clamping effect or so-called drawer effect. In order to increase the clamping force, i.e. the force, with which the clamping leg and bearing housing 4 are pressed against the pole 1, a tightening screw 31 is located at the upper frame portion. By tightening the screw 31, the upper portion of the frame is moved from the pole 1, and thereby the clamping leg 26 is clamped against one side of the pole at the same time as the bearing housing 4 is pressed against the opposite pole side, whereby the test device is retained safely. By pressing the bearing housing 4 against the pole, also the prerequisite condition for obtaining a correct measure of the rot depth and/or hardness is improved. The locking or clamping forces between the handle 25 and the sides 30 of the recess are also increased and result in a safe locking of the handle 25 in the recess 27.

In the embodiment shown in the drawing the handle 25 is straight and provided with graduation 32. In this way the clamping means 25,26 acts as a measuring callipers together with a pointer 33, which is located to the side of the recess 27 and in alignment with the side of the frame and/or bearing housing facing to the pole. When the test device has been clamped on a pole, the diameter of the pole can thus be read directly. By pressing the frame 2a from the pole by means of the tightening screw 31 in connection with the clamping of the test device, automatic compensation is made for the conical shape of the pole. The diameter measure, therefore, can be regarded to be the pole diameter at the test point. When higher accuracy is desired, the frame 2a can be provided with a level insensitive to impact or with a similar means, which directly indicates whether or not the frame inclines relative to the vertical plane.

According to the invention, the clamping leg 26 of the clamping means advantageously can be made of solid steel material or the like and can be formed with a pointed end 34 and a plane and 35 as shown in FIG. 7. The clamping means thereby also is a suitable tool in the form of a pick for removing possible wedge stones and earth prior to the driving of the test device down into the ground adjacent a pole. The clamping means also can be used for driving down the test device into the ground, when the end 35 is designed plane and a grip 36 is attached on the handle 25.

The present invention is not restricted to what is described above and shown in the drawings, but can be altered and modified in many different ways within the scope of the invention idea defined in the attached claims.

When the clamping means 25,26, for example, is designed also as a measuring callipers, the recess 27 suitably is placed substantially in parallel with the direction of test needle movement. Further, according to the invention the carrying arm 28 can be attached vertically movably on the frame 2a.

The principles, preferred embodiments and mode of operation of the present invention have been described in the foregoing specification. However, the invention which is intended to be protected is not to be construed as limited to the particular embodiments disclosed. The embodiments are to be regarded as illustrative rather than restrictive. Variations and changes may be made by others without departing from the spirit of the present invention. Accordingly, it is expressly intended that all such variations and changes which fall within the spirit and scope of the present invention as defined in the claims be embraced thereby.

What is claimed:

1. A device for testing the hardness or rot depth of a pole, comprising a frame portion, a penetration portion cooperating with the frame portion for penetrating into the pole material in response to an actuation force, actuator means exposed to actuations for producing the actuation force for the penetration portion, the frame portion includes a part which can be driven or sunk into the ground base of the pole adjacent the pole, the penetration portion being arranged on said part, said actuator means, when the part of the frame portion is driven entirely or partially into the ground base, including upper portions that extend above the ground surface so that said actuations can be applied for producing said actuation force, and indicating means arranged at an upper part of the frame portion for indicating the penetration of the penetration portion into the pole material for a definite magnitude of the actuation force.

2. The device as defined in claim 1, wherein the frame portion is oblong and carries at a lower end a bearing housing for said penetration portion.

3. The device as defined in claim 2, wherein the penetration portion includes a pointed needle-shaped member, which is longitudinally movable in the bearing housing, the needle-shaped member being attached to a rack, and said rack being longitudinally movable by a gear wheel.

4. The device as defined in claim 3, wherein the gear wheel is connected to a turning rod located in a bearing pipe, the bearing pipe is attached to the bearing housing and extends in parallel with and spaced from the side of the frame portion.

5. The device as defined in claim 4, wherein the actuator means comprises a dynamometric wrench, and wherein the turning rod projects upwardly from an upper end of the bearing pipe, the upwardly projecting portion of the turning rod is connected to the dynamometric wrench, said wrench producing the actuation force of the definite magnitude through the turning rod, the gear wheel and the rack.

6. The device as defined in claim 1, wherein the part of the frame portion to be driven into the ground base carried inclined wings which during the driving or sinking of the frame portion into the ground base force the frame portion inwardly toward the pole.

7. The device as defined in claim 1, further comprising clamping means for fixing the frame portion on the pole, said clamping means being arranged on the frame portion above the part to be driven into the ground base.

8. The device as defined in claim 4, wherein the indicating means comprise a graduated disc attached to the bearing pipe and an indication needle connected to the turning rod.

9. The device as defined in claim 1, further comprising an impact protection arranged at an upper end of the frame portion, said impact protection preventing undue impact effect on said indicating means.

10. The device as defined in claim 7, wherein the clamping means includes a handle and a clamping leg attached to an end of the handle, said clamping leg for engaging with the pole side remote from the frame portion, said handle being clamped detachably in a partially open recess in a carrying arm projecting from the frame portion, said clamping leg urging the frame portion toward the side of the pole.

11. The device as defined in claim 10, further comprising a tightening screw located at the upper part of the frame portion for pressing the frame portion outward from the pole after the clamping leg and frame portion have been pressed against the pole and the handle has been arranged in the recess, the tightening screw further increasing the clamping forces.

12. The device as defined in claim 10 or 11, wherein one side of the recess includes an indicating member, the handle being provided with a graduation extending from the clamping leg, said graduation co-operates with said indicating member for determining the pole diameter.

13. The device as defined in claim 10, wherein the clamping leg has a curved wedge shape, and said clamping leg together with the handle comprises a tool in the form of a pick.

14. The device as defined in claim 13, wherein the clamping leg is made of solid steel material and includes a plane end adapted for use as a striking tool.

* * * * *

UNITED STATES PATENT AND TRADEMARK OFFICE
CERTIFICATE OF CORRECTION

PATENT NO. : 4,343,179
DATED : Aug. 10, 1982
INVENTOR(S) : Gösta L. Åström and Sigvard N. Johansson It is certified that error appears in the above-identified patent and that said Letters Patent is hereby corrected as shown below:

Page 1, column 1, item [76], correct the inventor's name to read -- Gösta L. Åström --.

Signed and Sealed this

Twenty-sixth Day of February 1985

[SEAL]

Attest:

DONALD J. QUIGG

Attesting Officer

Acting Commissioner of Patents and Trademarks